United States Patent
Wakasone et al.

(10) Patent No.: US 12,070,186 B2
(45) Date of Patent: Aug. 27, 2024

(54) SURGICAL SYSTEM AND EXPANSION DEVICE

(71) Applicant: OLYMPUS CORPORATION, Tokyo (JP)

(72) Inventors: Jun Wakasone, Saitama (JP); Hiroyoshi Kobayashi, Tokyo (JP); Takeshi Murata, Tokyo (JP); Shotaro Takemoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 989 days.

(21) Appl. No.: 17/069,470

(22) Filed: Oct. 13, 2020

(65) Prior Publication Data
US 2021/0022723 A1    Jan. 28, 2021

Related U.S. Application Data

(63) Continuation of application No. PCT/JP2018/016972, filed on Apr. 26, 2018.

(51) Int. Cl.
*A61B 17/02*    (2006.01)
*A61B 1/00*    (2006.01)
(Continued)

(52) U.S. Cl.
CPC .......... *A61B 1/00135* (2013.01); *A61B 1/005* (2013.01); *A61B 1/018* (2013.01); *A61B 17/0218* (2013.01); *A61B 2017/00296* (2013.01)

(58) Field of Classification Search
CPC . A61B 17/0218; A61B 1/005; A61B 1/00135; A61B 1/01; A61B 1/018;
(Continued)

(56) References Cited

U.S. PATENT DOCUMENTS

| | | | | |
|---|---|---|---|---|
| 5,415,656 A | * | 5/1995 | Tihon | A61B 18/14 606/46 |
| 5,554,163 A | * | 9/1996 | Shturman | A61B 17/320783 606/159 |

(Continued)

FOREIGN PATENT DOCUMENTS

| | | |
|---|---|---|
| EP | 2 481 336 A1 | 8/2012 |
| EP | 2 481 355 A1 | 8/2012 |

(Continued)

OTHER PUBLICATIONS

International Search Report dated Jun. 19, 2018 received in International Application No. PCT/JP2018/016972, together with an English-language translation.

*Primary Examiner* — Anu Ramana
(74) *Attorney, Agent, or Firm* — Scully, Scott, Murphy & Presser, P.C.

(57) ABSTRACT

A surgical system includes: an overtube including a channel into which an endoscope is inserted; and an expansion device configured to ensure a surgical space by expanding an interior of a body at a distal side relative to a tip of the overtube. The expansion device includes a sheath and a wire configured to be protrudable from the sheath. The wire is configured to be switchable between a first configuration in which the wire protrudes from the sheath and a second configuration in which the wire protrudes from the sheath in a state where the wire is tilted, around a longitudinal axis, at an angle different from the first configuration.

12 Claims, 13 Drawing Sheets

(51) Int. Cl.
  *A61B 1/005* (2006.01)
  *A61B 1/018* (2006.01)
  *A61B 17/00* (2006.01)

(58) Field of Classification Search
  CPC .. A61B 2017/0237; A61B 2017/00292; A61B 2017/00296; A61B 17/320016; A61B 2017/32004; A61B 17/3207; A61B 17/320725; A61B 17/32075; A61B 17/32002; A61B 17/320758; A61B 2017/32006
  See application file for complete search history.

(56) References Cited

U.S. PATENT DOCUMENTS

| | | | |
|---|---|---|---|
| 6,022,362 A * | 2/2000 | Lee | A61B 10/0275 600/564 |
| 6,331,166 B1 * | 12/2001 | Burbank | A61B 90/17 606/45 |
| 6,863,676 B2 * | 3/2005 | Lee | A61B 10/0266 606/159 |
| 7,520,886 B2 * | 4/2009 | Surti | A61B 17/32002 30/91.2 |
| 10,537,238 B2 * | 1/2020 | Piskun | A61B 1/04 |
| 2001/0049509 A1 * | 12/2001 | Sekine | A61B 1/018 600/104 |
| 2005/0182417 A1 * | 8/2005 | Pagano | A61B 17/8811 606/92 |
| 2006/0106288 A1 | 5/2006 | Roth et al. | |
| 2006/0122462 A1 | 6/2006 | Roth et al. | |
| 2006/0184187 A1 * | 8/2006 | Surti | A61B 17/32002 606/170 |
| 2008/0091076 A1 | 4/2008 | Roth et al. | |
| 2008/0091077 A1 | 4/2008 | Roth et al. | |
| 2008/0091078 A1 | 4/2008 | Roth et al. | |
| 2008/0091079 A1 | 4/2008 | Roth et al. | |
| 2010/0191052 A1 * | 7/2010 | Surti | A61B 1/012 606/41 |
| 2010/0240952 A1 | 9/2010 | Okazaki et al. | |
| 2010/0280539 A1 | 11/2010 | Miyosi et al. | |
| 2010/0331619 A1 | 12/2010 | Miyoshi et al. | |
| 2011/0071342 A1 | 3/2011 | Okazaki et al. | |
| 2011/0092777 A1 | 4/2011 | Roth et al. | |
| 2011/0105848 A1 | 5/2011 | Sadovsky | |
| 2011/0190584 A1 | 8/2011 | Sugahara | |
| 2011/0190710 A1 | 8/2011 | Miyoshi et al. | |
| 2011/0224494 A1 | 9/2011 | Piskun et al. | |
| 2012/0083657 A1 | 4/2012 | Roth et al. | |
| 2013/0144118 A1 | 6/2013 | Piskun et al. | |
| 2013/0231534 A1 | 9/2013 | Piskun et al. | |
| 2013/0274553 A1 | 10/2013 | Piskun et al. | |
| 2013/0324795 A1 | 12/2013 | Nakajima et al. | |
| 2013/0345511 A1 | 12/2013 | Piskun et al. | |
| 2013/0345519 A1 | 12/2013 | Piskun et al. | |
| 2014/0142393 A1 | 5/2014 | Piskun et al. | |
| 2014/0371736 A1 | 12/2014 | Levin et al. | |
| 2015/0025314 A1 | 1/2015 | Piskun et al. | |
| 2015/0045825 A1 | 2/2015 | Caplan et al. | |
| 2015/0073215 A1 | 3/2015 | Nakajima | |
| 2015/0157192 A1 | 6/2015 | Piskun et al. | |
| 2015/0209024 A1 | 7/2015 | Piskun et al. | |
| 2015/0223798 A1 | 8/2015 | Piskun et al. | |
| 2015/0265818 A1 | 9/2015 | Piskun et al. | |
| 2015/0272564 A1 | 10/2015 | Piskun et al. | |
| 2015/0282800 A1 | 10/2015 | Piskun et al. | |
| 2015/0297209 A1 | 10/2015 | Piskun et al. | |
| 2015/0313584 A1 | 11/2015 | Piskun et al. | |
| 2015/0335324 A1 | 11/2015 | Piskun et al. | |
| 2016/0008050 A1 | 1/2016 | Rajagopalan et al. | |
| 2016/0015252 A1 | 1/2016 | Piskun et al. | |
| 2016/0051128 A1 | 2/2016 | Piskun et al. | |
| 2016/0081745 A1 | 3/2016 | Rajagopalan et al. | |
| 2016/0256663 A1 | 9/2016 | Rajagopalan et al. | |
| 2016/0278757 A1 | 9/2016 | Piskun et al. | |
| 2016/0309996 A1 | 10/2016 | Piskun et al. | |
| 2016/0310124 A1 | 10/2016 | Piskun et al. | |
| 2016/0338572 A1 | 11/2016 | Piskun et al. | |
| 2016/0354144 A1 | 12/2016 | Caplan et al. | |
| 2016/0374658 A1 | 12/2016 | Piskun | |
| 2017/0007324 A1 | 1/2017 | Kadamus et al. | |
| 2017/0079636 A1 | 3/2017 | Piskun et al. | |
| 2017/0135567 A1 | 5/2017 | Piskun et al. | |
| 2017/0196549 A1 | 7/2017 | Piskun et al. | |
| 2017/0251907 A1 | 9/2017 | Piskun et al. | |
| 2017/0325662 A1 | 11/2017 | Piskun et al. | |
| 2020/0001047 A1 | 1/2020 | Rajagopalan et al. | |
| 2020/0060758 A1 | 2/2020 | Rajagopalan et al. | |
| 2020/0138505 A1 | 5/2020 | Levin et al. | |

FOREIGN PATENT DOCUMENTS

| | | |
|---|---|---|
| EP | 2 481 377 A1 | 8/2012 |
| EP | 2 481 444 A1 | 8/2012 |
| EP | 2 679 169 A1 | 1/2014 |
| JP | H09-028665 A | 2/1997 |
| JP | 2002-52084 A | 2/2002 |
| JP | 2010-284503 A | 12/2010 |
| JP | 2015-516859 A | 6/2015 |
| JP | 2016-54774 A | 4/2016 |
| JP | 2016-526397 A | 9/2016 |
| WO | 2006/055804 A2 | 5/2006 |
| WO | 2009/047707 A2 | 4/2009 |
| WO | 2012/114569 A1 | 8/2012 |
| WO | 2013/146727 A1 | 10/2013 |
| WO | 2013/159066 A1 | 10/2013 |
| WO | 2014/200737 A1 | 12/2014 |

* cited by examiner

SURGICAL SYSTEM AND EXPANSION DEVICE

CROSS-REFERENCE TO RELATED APPLICATIONS

This is a continuation of International Application PCT/JP2018/016972, with an international filing date of Apr. 26, 2018, which is hereby incorporated by reference herein in its entirety.

TECHNICAL FIELD

The present invention relates to surgical systems and expansion devices.

BACKGROUND ART

A known system is provided with a retractor that ensures a visual field and a surgical field by spreading tissue disposed around an endoscope and a surgical tool guided by a flexible outer tube. This is achieved by causing a wire similarly guided by a flexible outer tube to protrude in a bent state at the distal ends of the endoscope and the surgical tool (e.g., see Patent Literature 1).

CITATION LIST

Patent Literature

{PTL 1}
Japanese Translation of PCT International Application, Publication No. 2016-526397

SUMMARY OF INVENTION

An aspect of the present invention is directed to a surgical system comprising: an overtube comprising a channel into which an endoscope is inserted; and an expansion device configured to ensure a surgical space by expanding an interior of a body at a distal side relative to a tip of the overtube, wherein the expansion device comprises: a sheath; and a wire configured to be protrudable from the sheath, wherein the wire is configured to be switchable between a first configuration in which the wire protrudes from the sheath and a second configuration in which the wire protrudes from the sheath in a state where the wire is tilted, around a longitudinal axis, at an angle different from the first configuration.

Another aspect of the present invention is directed to an expansion device configured to ensure a surgical space by expanding an interior of a body, the expansion device comprising: a sheath; and a wire configured to be protrudable from the sheath, wherein the wire is configured to be switchable between a first configuration in which the wire protrudes from the sheath and a second configuration in which the wire protrudes from the sheath in a state where the wire is tilted, around a longitudinal axis, at an angle different from the first configuration.

Another aspect of the present invention is directed to a lumen expanding method comprising: inserting an endoscope, an overtube, and an expansion device into a lumen, the expansion device being configured to ensure a surgical space by expanding an interior of a body; causing a wire to protrude radially outward from the expansion device at a distal side relative to a tip of the overtube; and rotating the wire around a longitudinal axis of the expansion device to change a protruding direction of the wire.

DESCRIPTION OF EMBODIMENTS

A surgical system 1 and an expansion device 4 according to an embodiment of the present invention will be described below with reference to the drawings.

Figure 1:
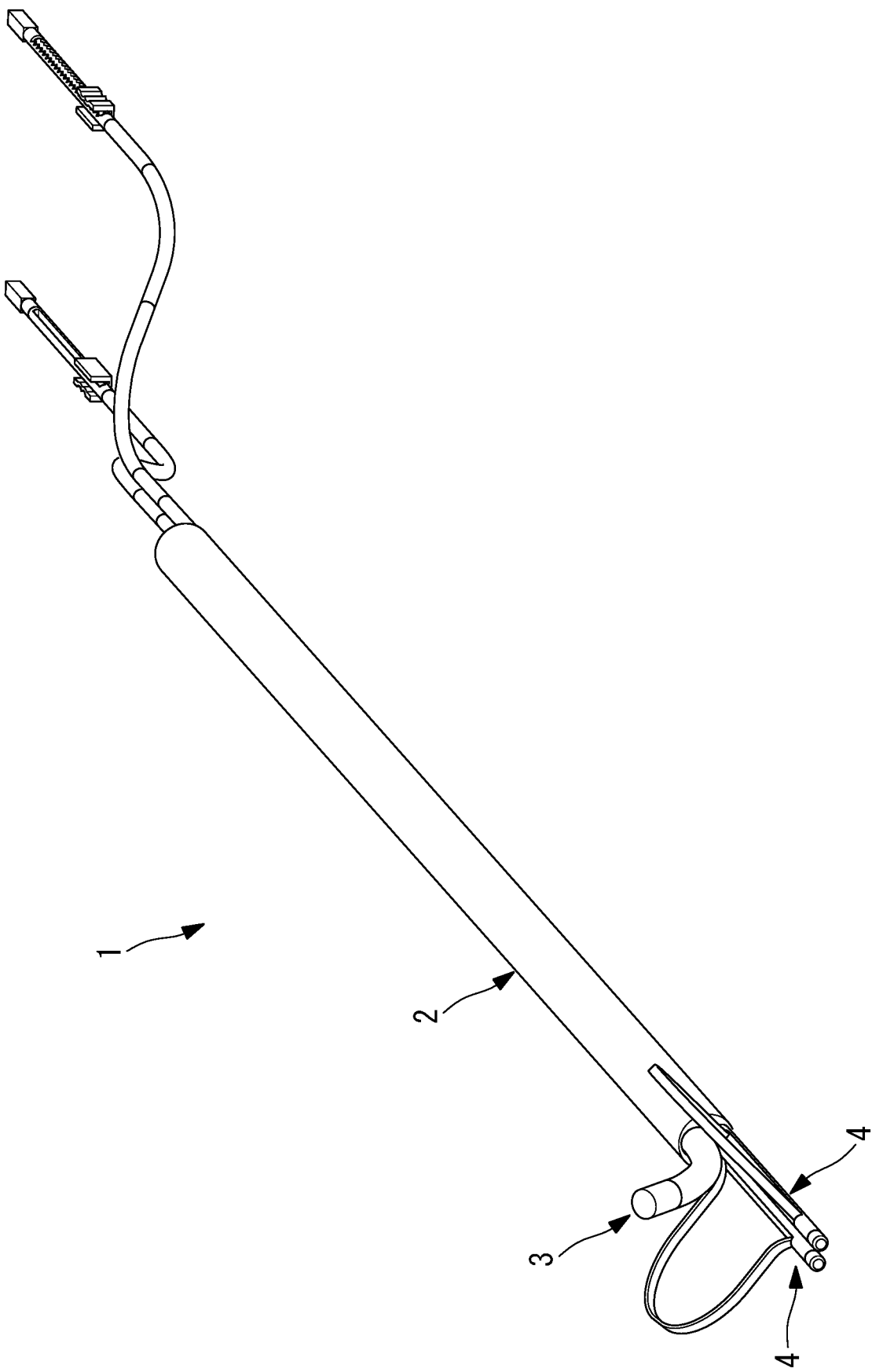
FIG. 1 is a perspective view illustrating a surgical system according to an embodiment of the present invention.
Figure 2:
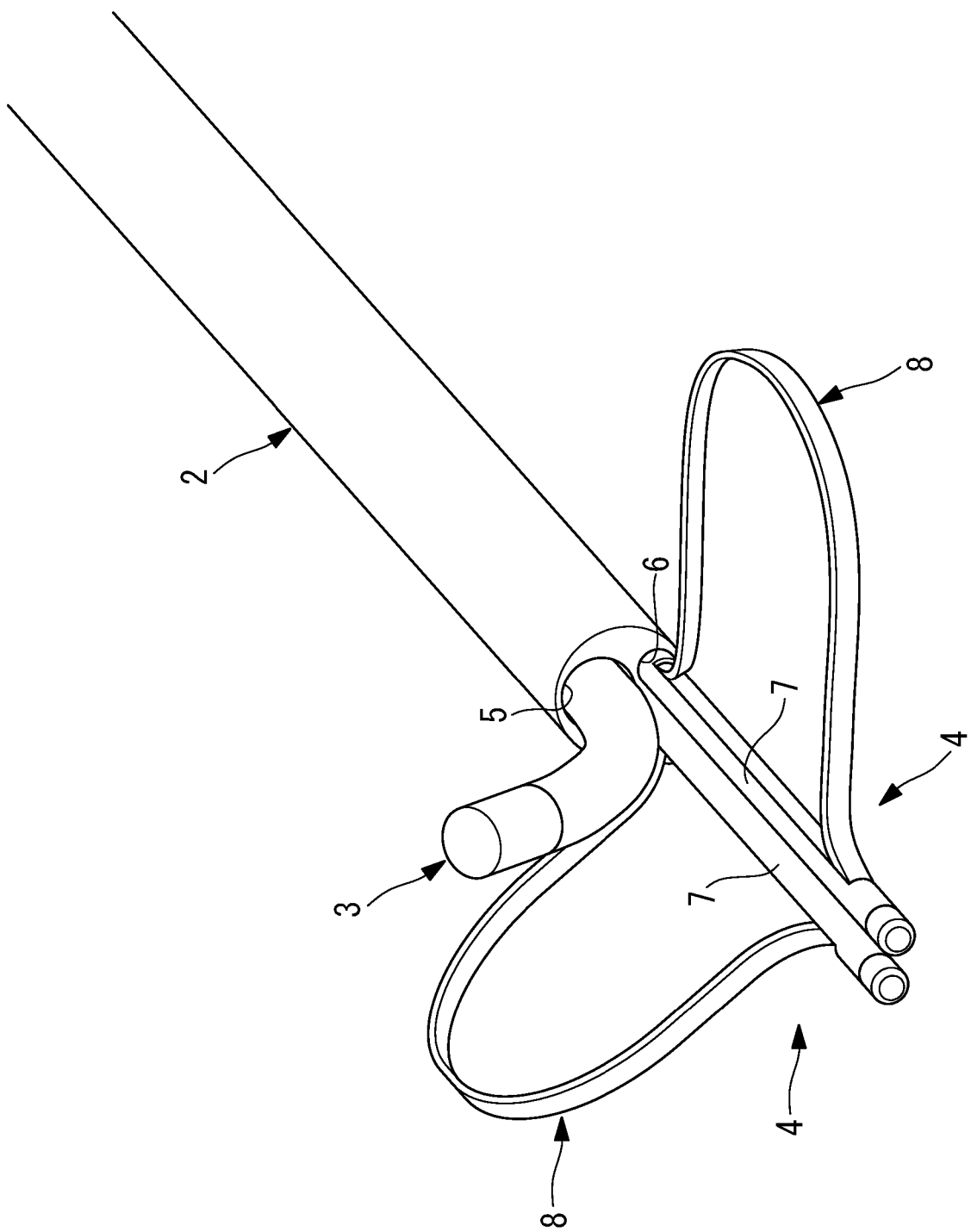
FIG. 2 is a partial perspective view illustrating the distal end of the surgical system in FIG. 1.

As shown in FIGS. 1 and 2, the surgical system 1 according to this embodiment includes a long flexible overtube 2, an endoscope 3 fitted in an endoscope channel 5 provided in the overtube 2, and two expansion devices 4 respectively fitted in two device channels 6 provided in the overtube 2.

The endoscope channel 5 has a circular cross-sectional shape with an inner dimension slightly larger than the outer dimension of the cross section of the endoscope 3. Each of the device channels 6 also has a circular cross-sectional shape with an inner dimension slightly larger than the outer dimension of a sheath 7 constituting each expansion device 4.

Figure 3:
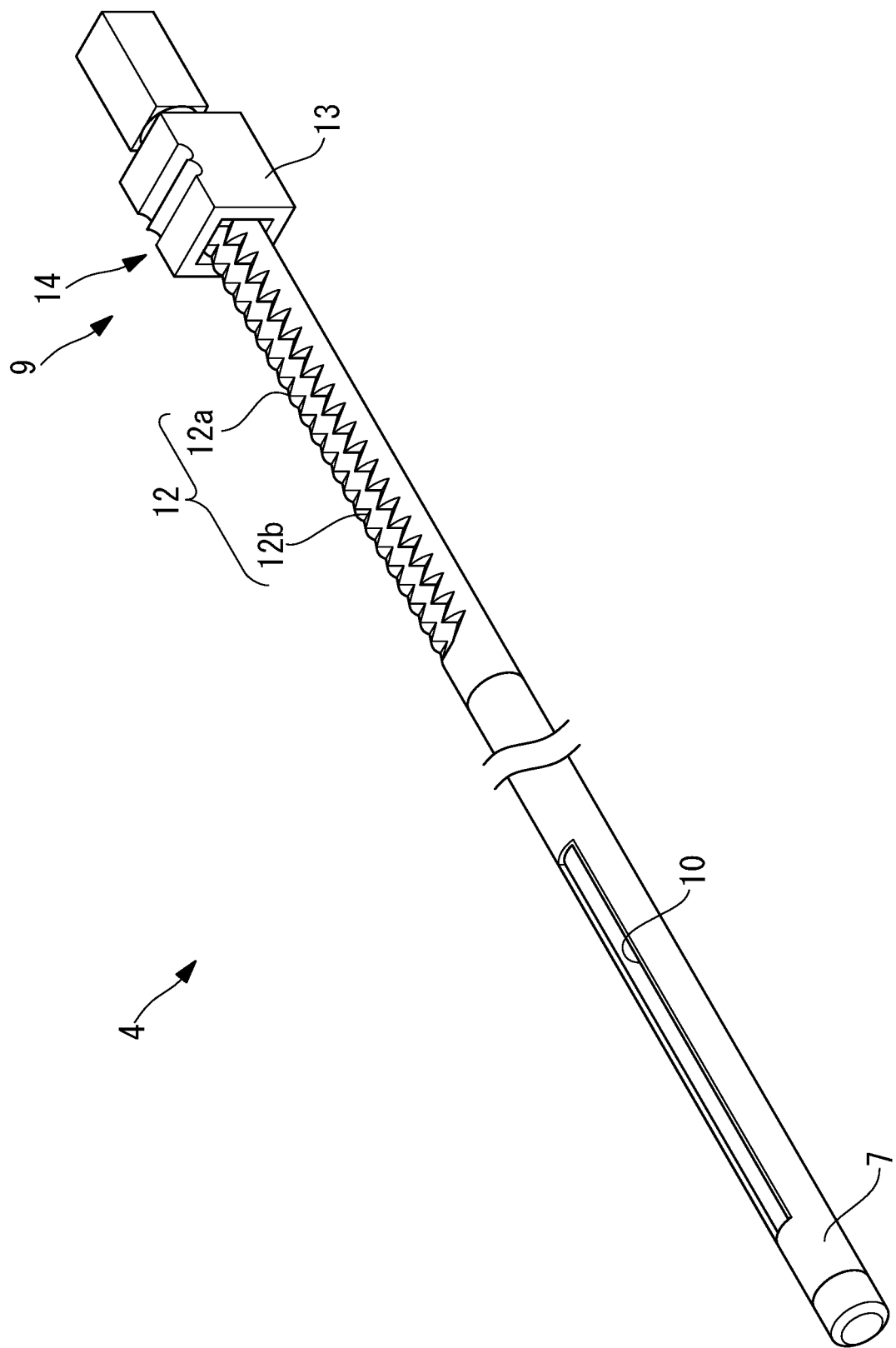
FIG. 3 is a perspective view illustrating one of expansion devices provided in the surgical system in FIG. 1.
Figure 4:
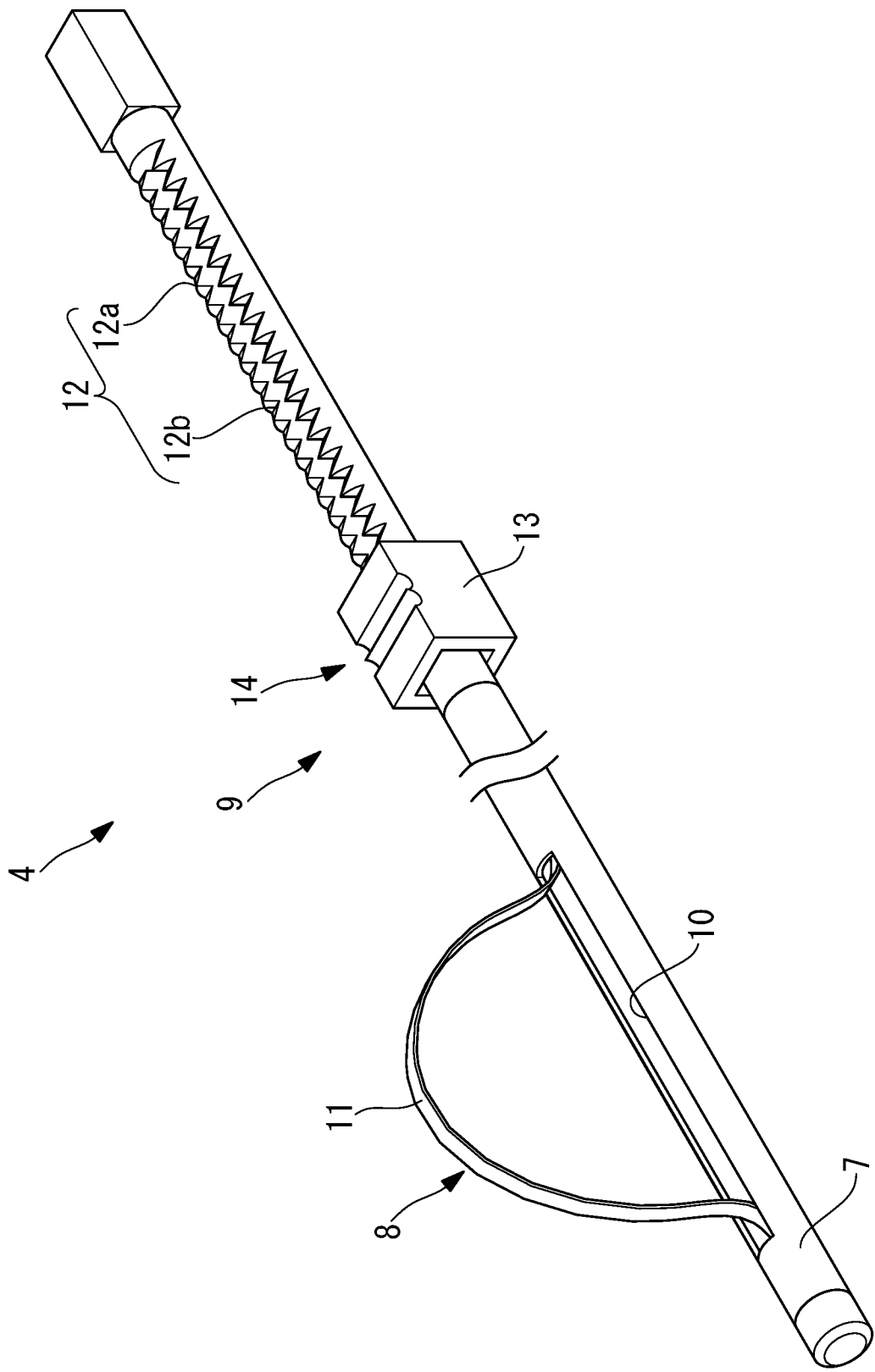
FIG. 4 is a perspective view illustrating a state where a wire of the expansion device in FIG. 3 protrudes from a slit.

As shown in FIGS. 3 and 4, each expansion device 4 includes a cylindrical sheath 7, a wire 8 accommodated in an inner hole 7a (see FIG. 7) of the sheath 7, and an operation member 9 provided at the proximal end of the sheath 7.

Because the sheath 7 having a circular cross-sectional shape is fitted in the device channel 6 having a circular cross-sectional shape, the sheath 7 can be rotated around the longitudinal axis within the device channel 6 by applying a rotational force around the longitudinal axis at the proximal end of the sheath 7.

The sheath 7 has a closed distal end and has a slit 10 located in one side surface toward the proximal end from the distal end and extending linearly in the longitudinal direction. The slit 10 extends radially through a wall surface constituting the sheath 7 and exposes the space in the inner hole 7a to the outside. The slit 10 has a fixed width in a direction orthogonal to the longitudinal direction.

The distal end of the wire 8 is fixed to the distal end of the sheath 7. The wire 8 includes a plate-like flat segment 11 near the distal end and a flexible segment (not shown) connected to the proximal end of the flat segment 11. The flat segment 11 has a width slightly smaller than the width of the slit 10 and a length that is sufficiently greater than the length of the slit 10. The flexible segment is capable of transmitting a compression force and a tensile force in the longitudinal direction, and has a bending rigidity lower than the bending rigidity of the flat segment 11.

The operation member 9 includes a ratchet mechanism 14 constituted of a serrated segment 12 provided at the proximal end of the sheath 7 and a slider 13 having an engaging section (not shown) therein that engages with the serrated segment 12 in a disengageable manner. With regard to the ratchet mechanism 14, the slider 13 can be moved toward the distal end relative to the sheath 7 by simply pushing the slider 13 forward. In contrast, the ratchet mechanism 14 can be locked such that the slider 13 cannot be moved toward the proximal end relative to the sheath 7 unless the engaging section and the serrated segment 12 are disengaged from each other.

The proximal end of the wire 8 is connected to the slider 13 of the operation member 9. Thus, when the slider 13 is moved toward the distal end relative to the sheath 7, a compression force is applied to the wire 8, so that the wire 8 is pushed forward. In addition, the engaging section of the slider 13 engages with one of recesses 12b of the serrated segment 12 at a position where the engaging section has passed over one of protrusions 12a of the serrated segment 12, so as to be locked in a state where the slider 13 does not move backward.

With regard to the wire 8 having received the compression force, a section thereof completely surrounded by the sheath 7 transmits the compression force without buckling, whereas the flat segment 11 is bent where the sheath 7 is provided with the slit 10, so that the bent segment protrudes radially outward from the slit 10.

Specifically, as the slider 13 is moved toward the distal end relative to the sheath 7, the flat segment 11 of the wire 8 is bent through the slit 10 so that the protruding amount can be increased outward in the radial direction, whereby a state where the wire 8 protrudes by a desired amount can be maintained by the ratchet mechanism 14. By disengaging the engaging section of the ratchet mechanism 14 and the serrated segment 12 from each other, the slider 13 can be moved toward the proximal end relative to the sheath 7, so that the protruding amount of the wire 8 can be reduced.

Figure 5:
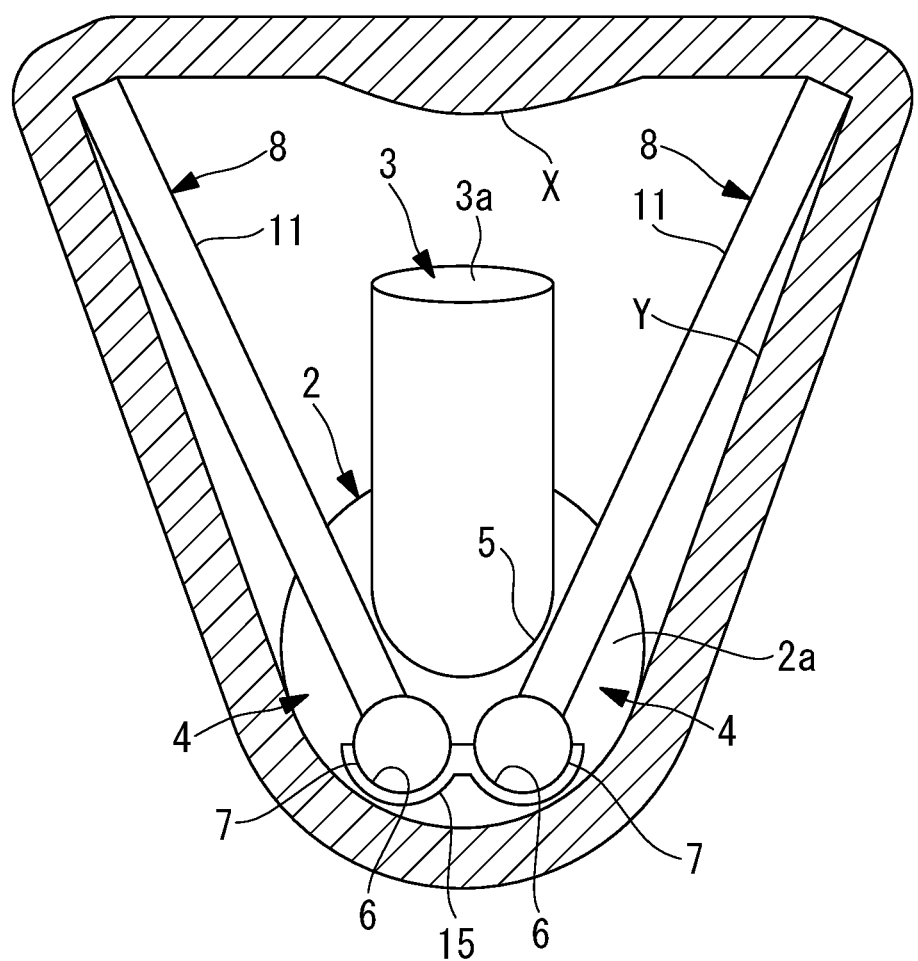
FIG. 5 is a cross-sectional view illustrating a state where tissue is expanded by reducing the angle between wires by using two expansion devices of the surgical system in FIG. 1.
Figure 6:
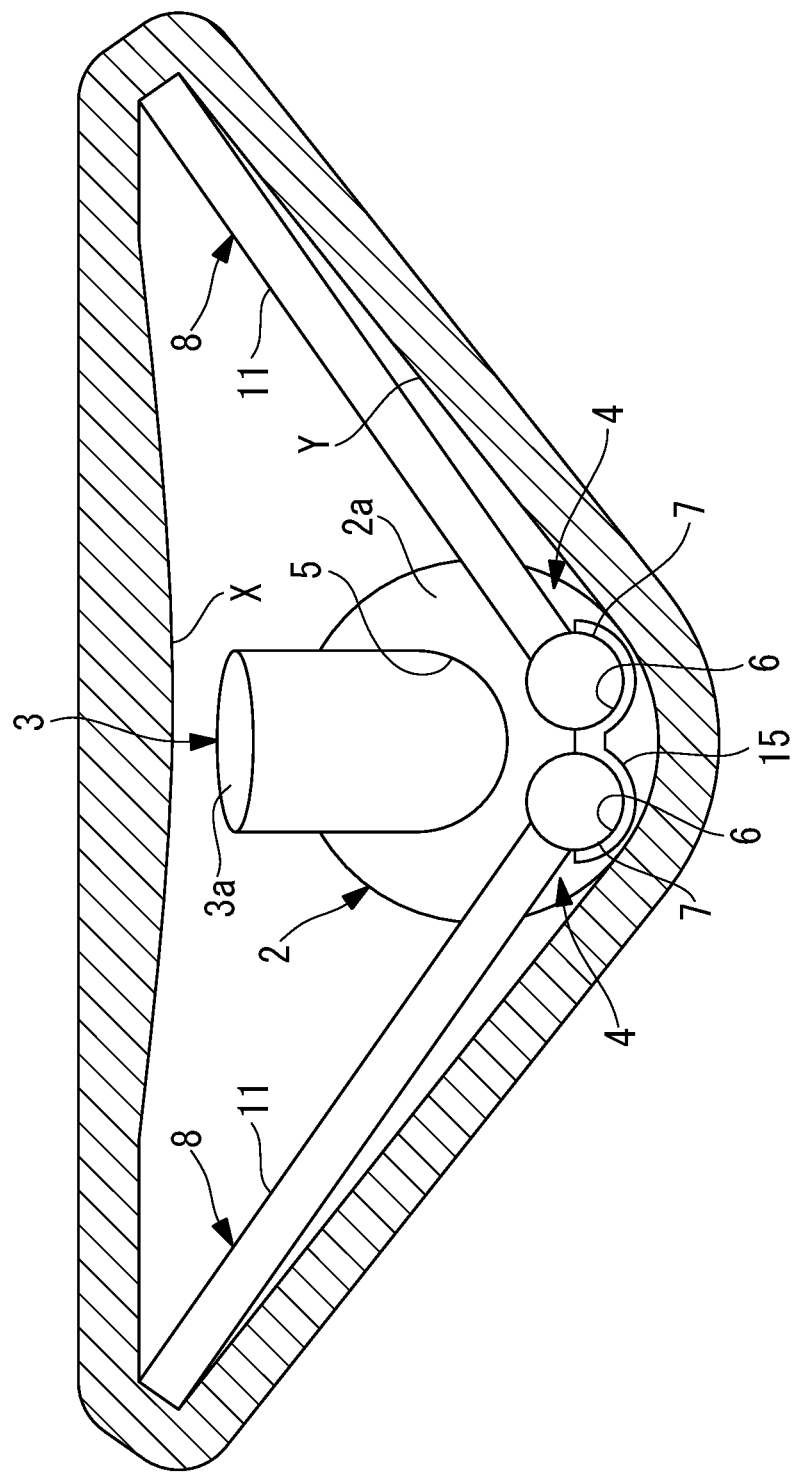
FIG. 6 is a cross-sectional view illustrating a state where tissue is expanded by increasing the angle between the wires by using the two expansion devices of the surgical system in FIG. 1.

As shown in FIGS. 5 and 6, the overtube 2 has a distal-end surface 2a provided with a rotation stopper 15 onto which the bent segments of the wires 8 protruding from the slits 10 abut in the circumferential direction. By bringing the wires 8 into abutment with the rotation stopper 15, the rotation stopper 15 regulates further rotation of the wires 8, thereby limiting the rotational angle range of the wires 8.

The operation of the surgical system 1 according to this embodiment having the above-described configuration will be described below.

In order to observe and treat an affected site X in a body cavity Y by using the surgical system 1 according to this embodiment, the endoscope 3 is inserted into the body cavity Y so that the endoscope 3 is disposed at a position where the affected site X in the body cavity Y can be checked in an image.

In this state, the overtube 2 is introduced into the body cavity Y from the proximal end of the endoscope 3 while using the endoscope 3 as a guide, up to a position where a bendable section at the distal end of the endoscope 3 protrudes from the distal-end surface 2a of the overtube 2. Subsequently, the expansion devices 4 are inserted through the device channels 6 from the proximal end of the overtube 2, until the slits 10 provided at the distal ends of the sheaths 7 of the expansion devices 4 entirely protrude forward from the distal-end surface 2a of the overtube 2.

In this state, the operation member 9 provided at the proximal end of each expansion device 4 is operated so that the slider 13 is moved toward the distal end relative to the sheath 7. Consequently, as shown in FIG. 4, the wire 8 is pushed forward by the slider 13, so that the flat segment 11 of the wire 8 protrudes in a bent state from the slit 10 protruding forward from the distal-end surface 2a of the overtube 2. Then, the bent section of the protruding flat segment 11 spreads out tissue in the body cavity Y located in front of the overtube 2, so that the space where a distal-end surface 3a of the endoscope 3 exists is expanded, as shown in FIG. 5.

For example, as shown in FIG. 5, the wires 8 of the two expansion devices 4 introduced through the two device channels 6 protrude at positions where they clamp the affected site X in the body cavity Y in the circumferential direction, so that the affected site X located between the two wires 8 can be maintained in an expanded state by being pulled in the circumferential direction. Then, as shown in FIG. 5, the bendable section of the endoscope 3 is bent to cause the distal-end surface 3a of the endoscope 3 to face the affected site X. This is advantageous in that the endoscope 3 can be maintained at an appropriate position relative to the affected site X, so that appropriate observation and surgery can be performed.

If the size of the affected site X in the body cavity Y is larger than the distance between the wires 8 in the state shown in FIG. 5, the two expansion devices 4 are rotated at the proximal end in opposite directions from each other around the longitudinal axis, thereby changing the angle between the wires 8 and thus increasing the distance between the wires 8, as shown in FIG. 6. Consequently, even in a case where the affected site X is large, the affected site X can be pulled and be maintained in an expanded state by using the two wires 8. This is advantageous in that appropriate observation and surgery can be performed using the endoscope 3.

The distance between the distal-end surface 3a of the endoscope 3 and the affected site X can also be appropriately adjusted by adjusting not only the protruding amount of the endoscope 3 but also the protruding amount of the wires 8.

Furthermore, although the operation for rotating each expansion device 4 is performed at the proximal end of the expansion device 4, since the rotational angle of the wire 8 is limited by causing the wire 8 protruding from the slit 10 to abut on the rotation stopper 15 provided at the distal-end surface 2a of the overtube 2, excessive rotation of the wire 8 can be prevented without having to control the rotational angle at the proximal end of the expansion device 4.

Figure 7:
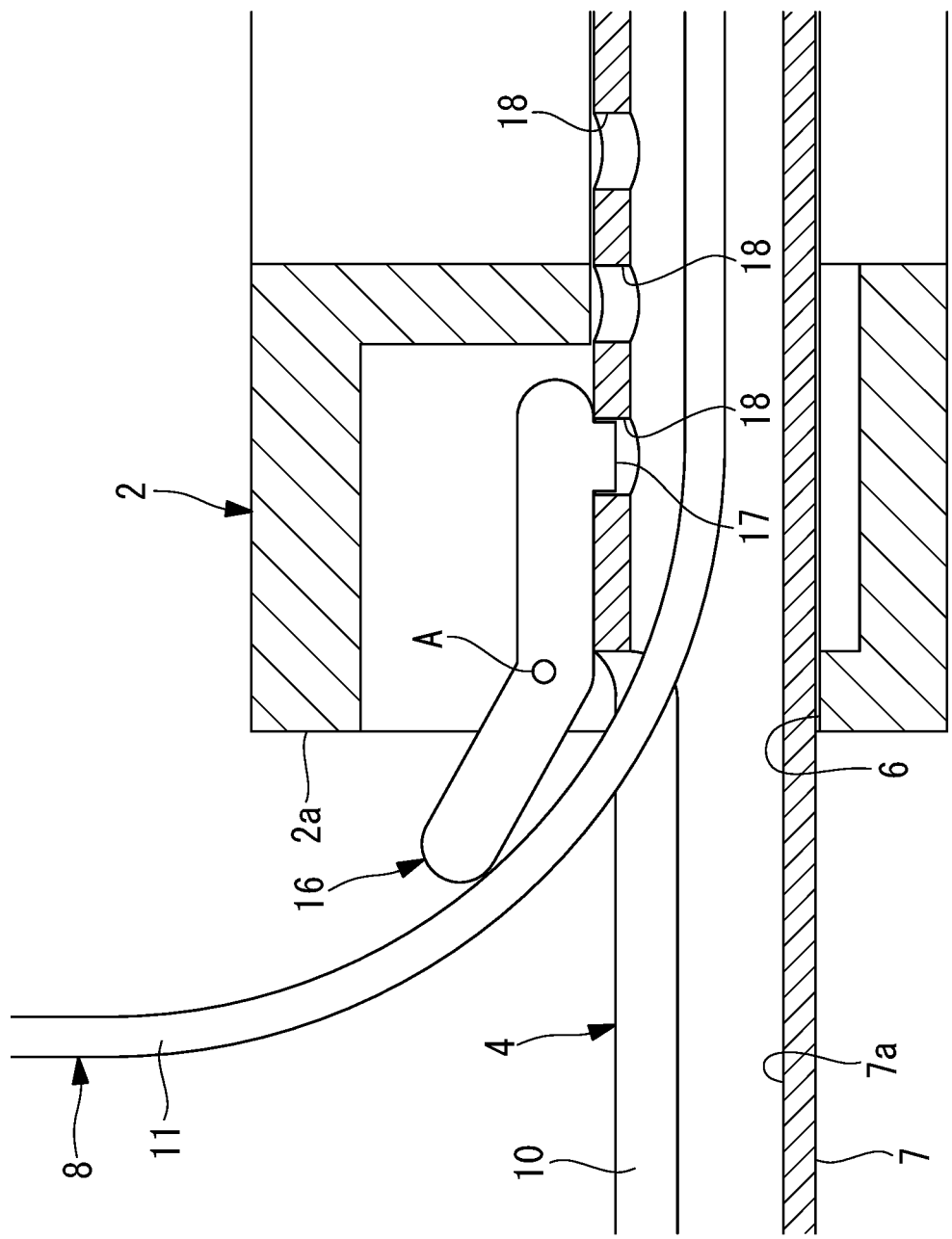
FIG. 7 is a partial vertical-sectional view illustrating a retraction prevention stopper provided in a modification of the surgical system in FIG. 1.
Figure 8:
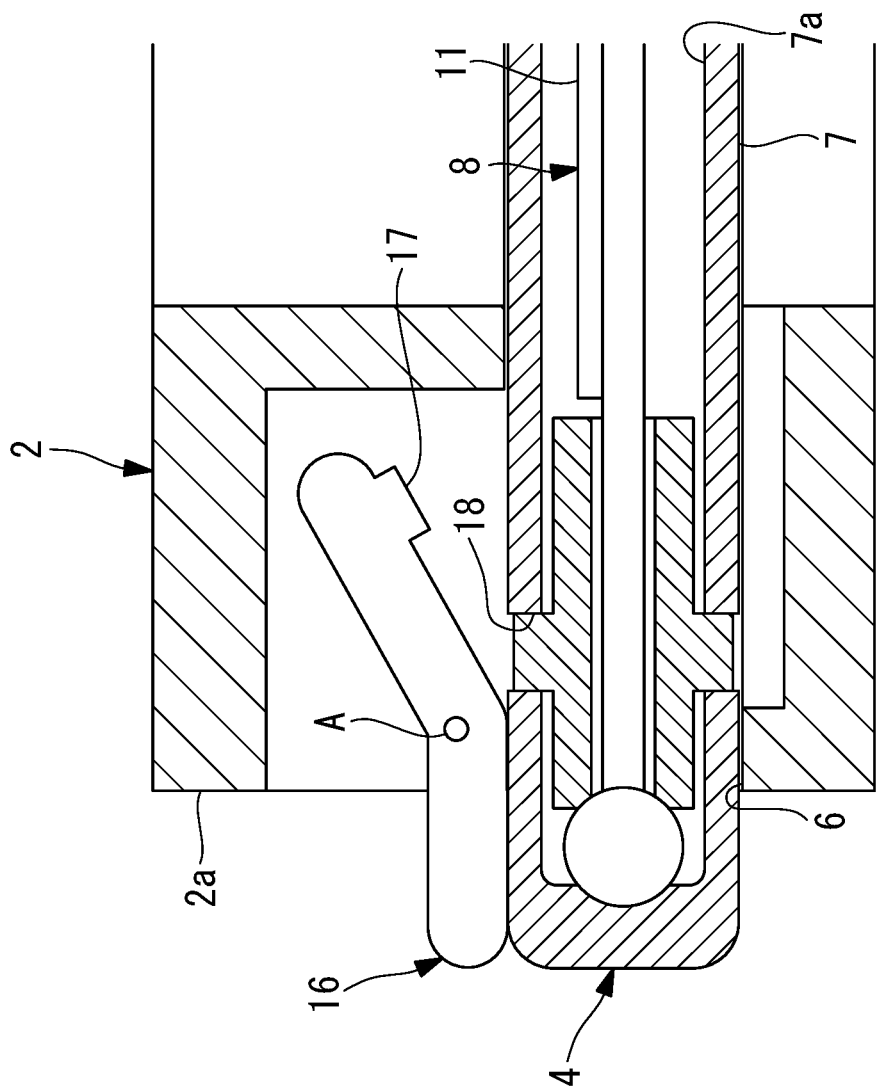
FIG. 8 is a partial vertical-sectional view illustrating a state where an engagement by the retraction prevention stopper in FIG. 7 has been canceled.

As shown in FIGS. 7 and 8, in this embodiment, a lever (retraction prevention stopper) 16 supported in a swivelable manner around an axis A extending parallel to the radial direction of the overtube 2 may be disposed on the overtube 2, and recesses 18 engageable with a protrusion 17 provided at the lever 16 may be provided toward the proximal end, relative to the slit 10, of the sheath 7 of the expansion device 4. It is preferable that a plurality of recesses 18 be provided at intervals in a direction parallel to the longitudinal axis of the sheath 7.

Accordingly, when the sheath 7 is pulled toward the proximal end in a state where the bent segment of the wire 8 protrudes through the slit 10, the proximal end of the bent segment of the wire 8 comes into contact with the lever 16 to swivel the lever 16, as shown in FIG. 7, so that the protrusion 17 of the lever 16 moves into engagement with one of the recesses 18 in the sheath 7, thereby preventing the sheath 7 from being retracted any further.

Specifically, since the expansion device 4 cannot be retracted into the device channel 6 when the wire 8 remains protruding from the slit 10, this state is maintained to advantageously prevent the wire 8 and the device channel 6 from being damaged.

The lever 16 is biased by a spring (not shown) in a direction for disengaging the recess 18 and the protrusion 17 from each other, so that when the wire 8 is retracted into the slit 10, the engagement is canceled by the spring (not shown), as shown in FIG. 8, whereby the expansion device 4 can be retracted into the device channel 6.

Figure 9:
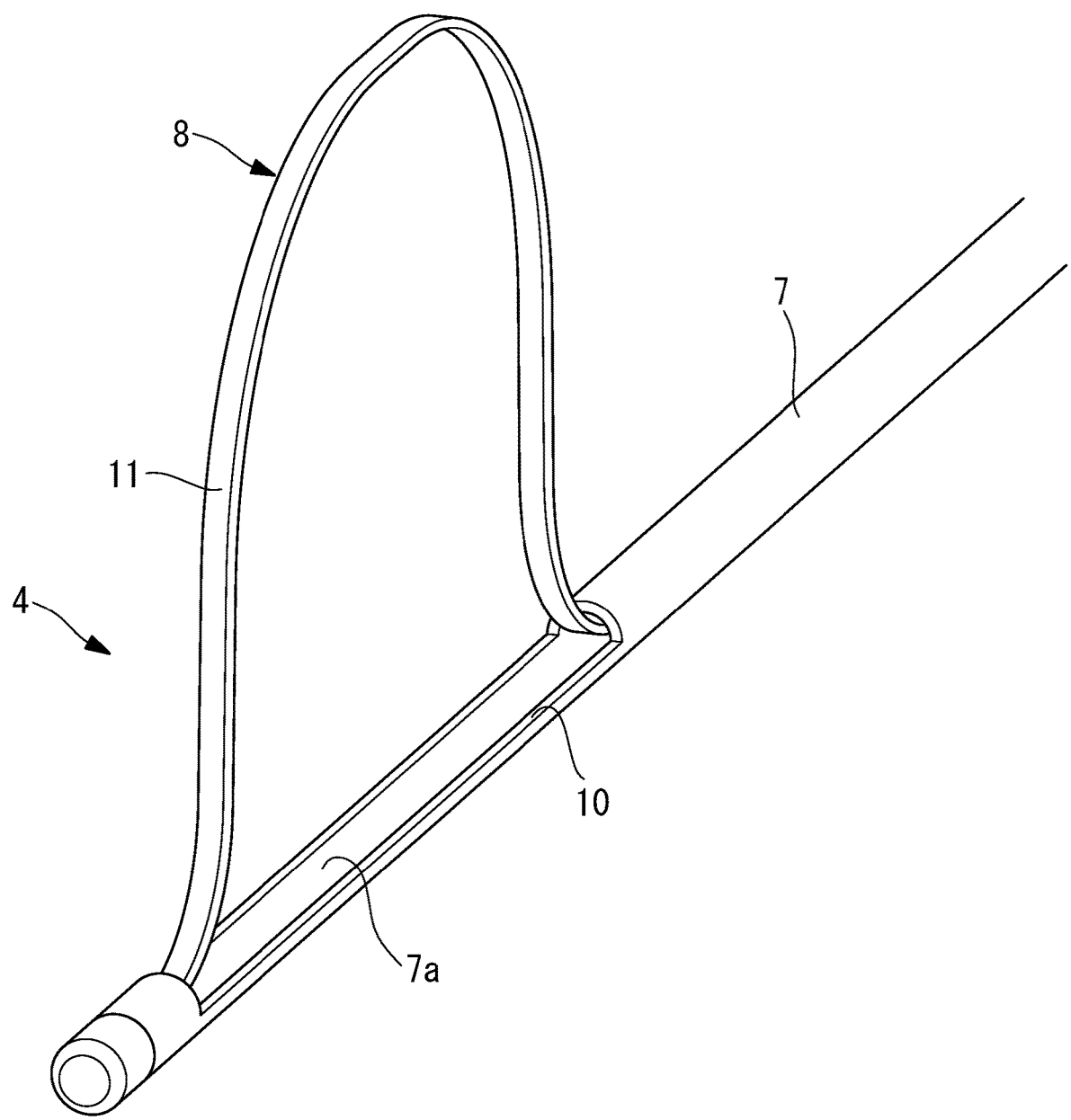
FIG. 9 is a partial perspective view illustrating a modification of each expansion device provided in the surgical system in FIG. 1.
Figure 10:
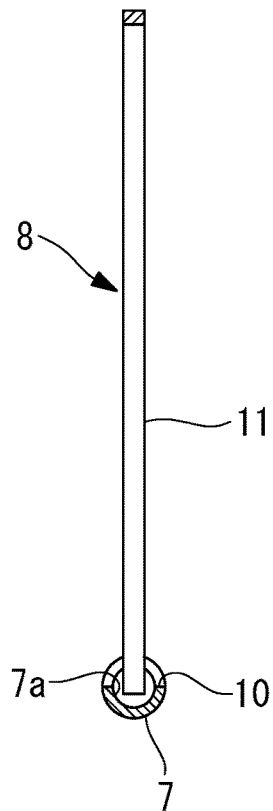
FIG. 10 is a cross-sectional view of a slit in the expansion device in FIG. 9.
Figure 11:
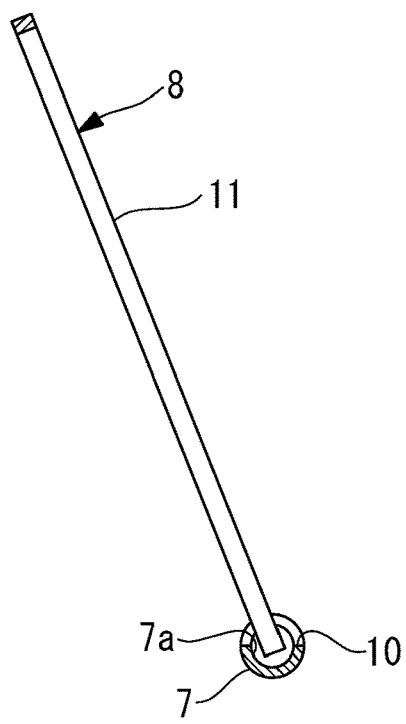
FIG. 11 is a cross-sectional view of the slit, illustrating a state where the wire of the expansion device in FIG. 9 is rotated.
Figure 12:
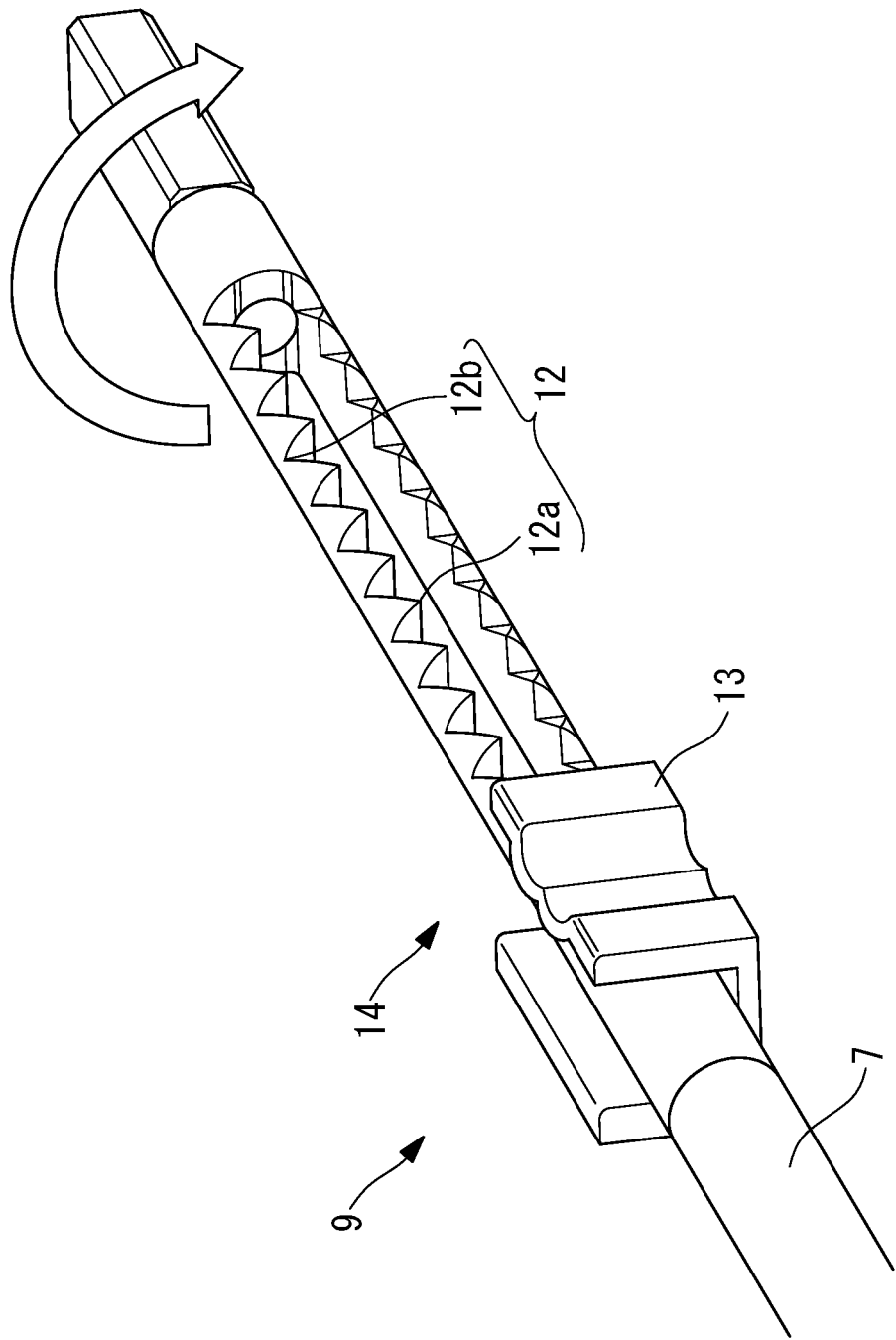
FIG. 12 is a partial perspective view illustrating the proximal end of the expansion device in FIG. 9.

As an alternative to this embodiment in which the width of the slit 10 is set to be slightly larger than the width of the flat segment 11, the slit 10 may be set to be sufficiently wider than the flat segment 11, as shown in FIG. 9. Consequently, as shown in FIGS. 10 and 11, the angle of the wire 8 can be changed by rotating the wire 8 within the sheath 7. In this case, as shown in FIG. 12, the entire ratchet mechanism 14 provided at the proximal end of the expansion device 4 may be provided in a rotatable manner around the longitudinal axis relative to the sheath 7, so that the wire 8 can be rotated in accordance with the rotation of the ratchet mechanism 14.

Figure 13:
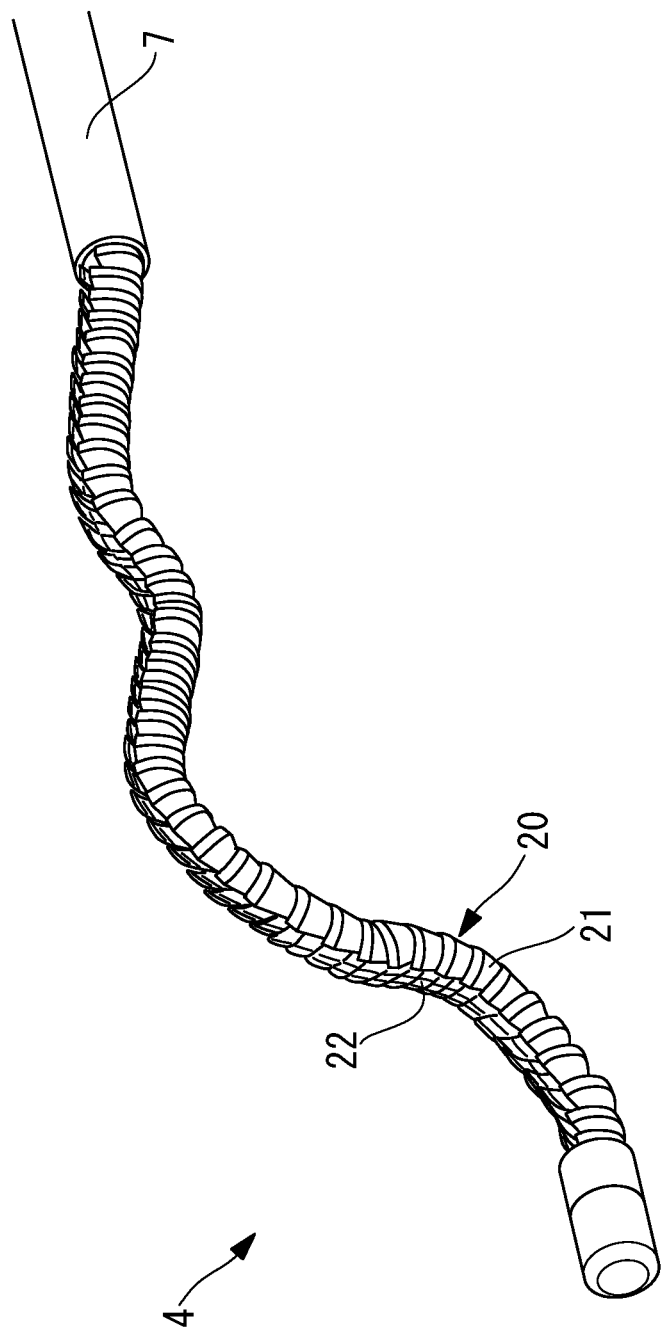
FIG. 13 is a perspective view of a modification of the expansion device in FIG. 9, illustrating a state where a plurality of components constituting the distal end of a sheath are moved away from each other.
Figure 14:
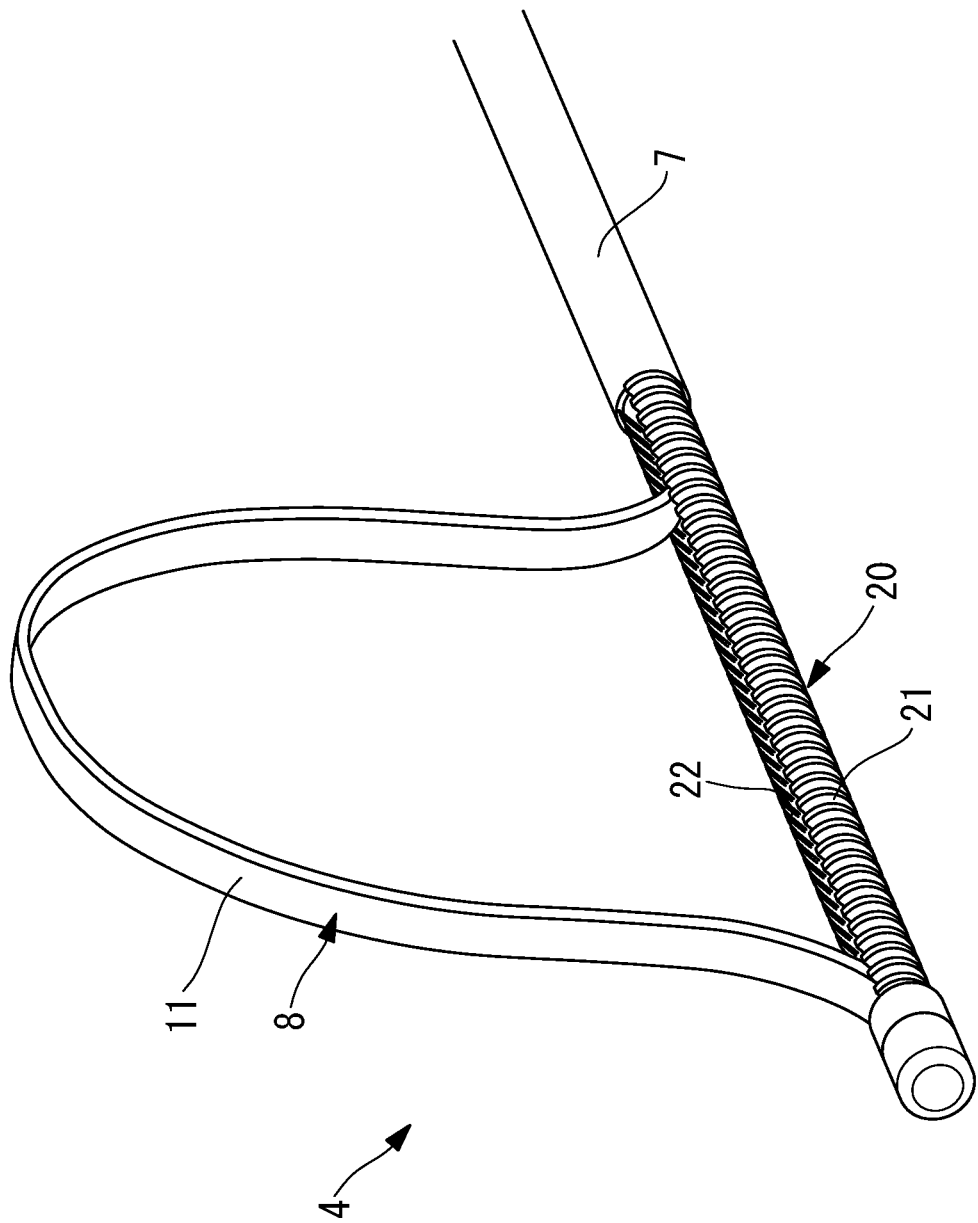
FIG. 14 is a perspective view illustrating a state where the components in FIG. 13 are moved into contact with each other.

In this embodiment, the sheath 7 requires rigidity to a certain extent for maintaining the wire 8 protruding from the slit 10 in a bent state. Alternatively, as shown in FIGS. 13 and 14, the distal end of the sheath 7 may be constituted of a deformable unit 20 having a plurality of components 21 that can be moved into contact with each other and away from each other in the axial direction by operating a wire (not shown) different from the wire 8.

Each component 21 is obtained by cutting out a part of a short cylindrical component in the circumferential direction so as to be cross-sectionally C-shaped. As shown in FIG. 14, the components 21 are moved into contact with each other so as to form a highly-rigid tube having a set of slits 22. On the other hand, as shown in FIG. 13, by being moved away from each other, the components 21 can be reduced in rigidity and can be bent freely. When the components 21 are to be inserted into the device channel 6, the components 21 bend readily in conformity to the bent shape of the device channel 6. This is advantageous in that the resistance at the time of insertion can be reduced, thereby achieving improved ease of insertion.

Furthermore, as an alternative to this embodiment in which the segment of the wire 8 protruding from the slit 10 is flat for higher bendability in one direction, the flat segment 11 may have a cross-sectionally elliptical or oval shape with a long diameter and a short diameter. Moreover, the wire 8 does not have to be provided with the flat segment 11 if the slit 10 can act as a guide in the bending direction.

Furthermore, as an alternative to this embodiment in which two device channels 6 and two expansion devices 4 are used, a single device channel 6 and a single expansion device 4 may be used.

As a result, the above-described embodiment leads to the following aspects.

An aspect of the present invention is directed to a surgical system including an overtube, an endoscope inserted in an endoscope channel provided in the overtube such that the endoscope is protrudable from a distal-end surface of the overtube, and an expansion device inserted in a device channel provided in the overtube such that the expansion device is protrudable from the distal-end surface of the overtube. The expansion device includes a tubular sheath inserted in the device channel in a movable manner in a longitudinal direction, a wire that is accommodated in the sheath and whose distal end is attached to a distal end of the sheath, and an operation member that is connected to a proximal end of the wire and that moves the proximal end in the longitudinal direction relative to the sheath. The sheath has a slit that is located near the distal end of the sheath and that extends through a wall surface of the sheath in a radial direction over a predetermined range in the longitudinal direction. The slit has a width that allows a bent segment of the wire, which is bent by operating the operation member, to extend therethrough. In a state where the bent segment protrudes outward from the sheath through the slit, the wire is rotatable around an axis extending in a longitudinal direction of the device channel.

According to this aspect, the overtube is inserted into the body, the endoscope is inserted through the endoscope channel provided in the overtube, the expansion device is inserted through the device channel provided in the overtube, and the distal end of the endoscope and the distal end of the expansion device protrude from the distal-end surface of the overtube.

When the operation member of the expansion device is operated in this state to move the operation member toward the distal end relative to the sheath, the wire whose proximal end is connected to the operation member is pressed toward the distal end. Because the sheath is provided with the slit at the distal end thereof, the wire receiving a compression force bends toward the slit. The bent segment protrudes outward from the sheath through the slit, whereby tissue disposed near the distal end of the endoscope is pressed and spread out.

Then, the tissue pressed by the wire of the expansion device is maintained in a pulled state by being hooked to the wire, thereby facilitating the observation and surgery of an affected site using the endoscope.

In the above aspect, the device channel may include two device channels provided in the overtube, and each of the device channels may be provided with the expansion device.

Accordingly, by rotating the wire of at least one of the expansion devices around the longitudinal axis of the corresponding device channel, the distance between the two wires can be adjusted. Consequently, the distance between the wires may be increased if the affected site is large, or the distance between the wires may be reduced if the affected site is small, whereby the visual field and the surgical field can be adjusted in accordance with the size of the affected site to be treated.

Furthermore, in the above aspect, at least a part of the wire in the longitudinal direction thereof may be provided with a flat segment having a flat cross-sectional shape.

Accordingly, the flat segment can be bent in one direction with the smaller bending rigidity in accordance with a compression force applied to the wire by the operation member connected to the proximal end of the wire. Consequently, means for guiding the wire in the bending direction is not necessary, whereby the wire can protrude accurately in a desired direction.

Furthermore, in the above aspect, the wire may be attached in a rotatable manner around a longitudinal axis within the sheath.

Accordingly, the distance between wires can be adjusted by fixing the sheath and simply rotating the wire around the longitudinal axis.

Furthermore, in the above aspect, the wire may include a flexible segment located at a proximal end of the flat segment and having a bending rigidity lower than a minimum bending rigidity of the flat segment.

Accordingly, the bending rigidity of the expansion device can be reduced, and the sheath and the wire can be deformed in conformity to the device channel of the bent overtube.

Furthermore, in the above aspect, a distal end of the sheath may be provided with a deformable unit having a plurality of cross-sectionally C-shaped components that are movable into contact with each other and away from each other in the longitudinal direction, and the slit may be formed as a result of the components being in contact with each other.

Accordingly, when the expansion device is to be inserted into the device channel, the plurality of components constituting the deformable unit are moved away from each other to increase bendability, thereby facilitating the insertion process. In contrast, when tissue is to be expanded by using the wire, the plurality of components constituting the deformable unit are moved into contact with each other in the longitudinal direction. Since each component is C-shaped in cross section, a set of slits is formed as a result of moving the components into contact with each other. Consequently, the bent segment of the wire in the sheath protrudes outward through the slit, thereby expanding the tissue.

Furthermore, in the above aspect, the surgical system may further include a retraction prevention stopper that regulates retraction of the sheath into the device channel in a state where the bent segment of the wire extends through the slit and protrudes outward from the sheath.

Accordingly, in a state where the bent segment of the wire extends through the slit and protrudes outward from the sheath, the retraction prevention stopper can prevent the wire from being damaged as a result of the sheath being retracted into the device channel.

Furthermore, in the above aspect, the overtube may be provided with a rotation stopper that limits a rotational angle of the wire in a state where the bent segment of the wire extends through the slit and protrudes outward from the sheath.

Accordingly, even without having to monitor the amount of rotation of the wire at the proximal end of the wire, the angle of the wire can be set by rotating the wire until it abuts on the rotation stopper.

Another aspect of the present invention is directed to an expansion device that is inserted into a body and expands a body cavity. The expansion device includes a tubular sheath, a wire that is accommodated in the sheath and whose distal end is attached to a distal end of the sheath, and an operation member that is connected to a proximal end of the wire and that moves the proximal end in a longitudinal direction thereof relative to the sheath. The sheath has a slit that is located at a proximal end of the sheath relative to a distal end thereof and that extends in the longitudinal direction through a wall surface of the sheath in a radial direction. The slit has a width that allows a bent segment of the wire, which is bent by operating the operation member, to extend therethrough. In a state where the bent segment protrudes outward from the sheath through the slit, the wire is rotatable around an axis extending in the longitudinal direction thereof relative to the sheath.

In the above aspect, at least a part of the wire in the longitudinal direction thereof may be provided with a flat segment having a flat cross-sectional shape.

Furthermore, in the above aspect, the wire may include a flexible segment located at a proximal end of the flat segment and having a bending rigidity lower than a minimum bending rigidity of the flat segment.

Moreover, in the above aspect, a distal end of the sheath may be provided with a deformable unit having a plurality of cross-sectionally C-shaped components that are movable into contact with each other and away from each other in the longitudinal direction, and the slit may be formed as a result of the components being in contact with each other.

The present invention is advantageous in that a visual field and an surgical field can be adjusted in accordance with the size of an affected site to be treated.

REFERENCE SIGNS LIST 1 surgical system
2 overtube
2a distal-end surface
3 endoscope
4 expansion device
5 endoscope channel
6 device channel
7 sheath
8 wire
9 operation member
10, 22 slit
11 flat segment
15 rotation stopper
16 lever (retraction prevention stopper)
20 deformable unit
21 component

The invention claimed is:

1. A surgical system comprising:
an overtube comprising a channel into which an endoscope is inserted;
an expansion device configured to ensure a surgical space by expanding an interior of a body, the expansion device disposed at a distal side relative to a tip of the overtube,
wherein the expansion device comprises:
a sheath; and
a wire configured to be protrudable from the sheath, and
an operation member comprising a ratchet mechanism for adjusting a position of a proximal end of the wire,
the wire is configured to be switchable between a first configuration in which the wire protrudes from the sheath and a second configuration in which the wire protrudes from the sheath in a state where the wire is tilted, around a longitudinal axis, at an angle different from the first configuration;

the wire switches from the first configuration to the second configuration by rotating about a longitudinal axis of the sheath; and
the operation member is configured to rotate the wire about the longitudinal axis of the sheath.

2. The surgical system according to claim 1, wherein the overtube further comprises a first stopper for preventing the wire from being retracted by a predetermined length in a direction toward the distal side of the overtube.

3. The surgical system according to claim 2, wherein the overtube further comprises a second stopper for preventing the wire and the sheath from rotating by a predetermined angle when the wire and the sheath rotate together relative to a longitudinal direction of the overtube.

4. A surgical system comprising:
an overtube comprising a channel into which an endoscope is inserted; and
an expansion device configured to ensure a surgical space by expanding an interior of a body, the expansion device disposed at a distal side relative to a tip of the overtube,
wherein the expansion device comprises:
a sheath; and
a wire configured to be protrudable from the sheath,
the wire is configured to be switchable between a first configuration in which the wire protrudes from the sheath and a second configuration in which the wire protrudes from the sheath in a state where the wire is tilted, around a longitudinal axis, at an angle different from the first configuration; and
the wire switches from the first configuration to the second configuration by the wire and the sheath rotating together about a longitudinal axis of the sheath.

5. The surgical system according to claim 4, further comprising:
an operation member having a ratchet mechanism capable of adjusting a position of a proximal end of the wire,
wherein the operation member is configured to be capable of rotating the wire and the sheath together about the longitudinal axis of the sheath.

6. A surgical system comprising:
an overtube comprising a channel into which an endoscope is inserted; and
an expansion device configured to ensure a surgical space by expanding an interior of a body, the expansion device disposed at a distal side relative to a tip of the overtube,
wherein the expansion device comprises:
a sheath; and
a wire configured to be protrudable from the sheath,
the wire is configured to be switchable between a first configuration in which the wire protrudes from the sheath and a second configuration in which the wire protrudes from the sheath in a state where the wire is tilted, around a longitudinal axis, at an angle different from the first configuration;
the sheath comprises a slit through which the wire protrudes;
the wire comprises a flat segment having a flat cross-sectional shape, and
a length of the flat segment in a longitudinal direction is greater than a length of a long side of the slit.

7. The surgical system according to claim 6, wherein the wire includes a flexible segment located at a proximal end of the flat segment and having a bending rigidity lower than a minimum bending rigidity of the flat segment.

8. The surgical system according to claim 6, wherein a distal end of the sheath is provided with a plurality of cross-sectionally C-shaped components that are movable into contact with each other and away from each other in a longitudinal direction of the sheath, and the slit is formed by the plurality of components being in contact with each other.

9. An expansion device configured to ensure a surgical space by expanding an interior of a body, the expansion device comprising:
a sheath;
a wire configured to be protrudable from the sheath, and
an operation member comprising a ratchet mechanism for adjusting a position of a proximal end of the wire,
wherein the wire is configured to be switchable between a first configuration in which the wire protrudes from the sheath and a second configuration in which the wire protrudes from the sheath in a state where the wire is tilted, around a longitudinal axis, at an angle different from the first configuration;
the wire switches from the first configuration to the second configuration by rotating about a longitudinal axis of the sheath; and
the operation member is configured to rotate the wire about the longitudinal axis of the sheath.

10. An expansion device configured to ensure a surgical space by expanding an interior of a body, the expansion device comprising:
a sheath; and
a wire configured to be protrudable from the sheath,
wherein the wire is configured to be switchable between a first configuration in which the wire protrudes from the sheath and a second configuration in which the wire protrudes from the sheath in a state where the wire is tilted, around a longitudinal axis, at an angle different from the first configuration; and
the wire switches from the first configuration to the second configuration as a result of the wire and the sheath rotating together about a longitudinal axis of the sheath.

11. The expansion device according to claim 10, further comprising:
an operation member having a ratchet mechanism configured to adjust a position of a proximal end of the wire,
wherein the operation member is configured to rotate the wire and the sheath together about the longitudinal axis of the sheath.

12. An expansion device configured to ensure a surgical space by expanding an interior of a body, the expansion device comprising:
a sheath;
a wire configured to be protrudable from the sheath,
wherein the wire is configured to be switchable between a first configuration in which the wire protrudes from the sheath and a second configuration in which the wire protrudes from the sheath in a state where the wire is tilted, around a longitudinal axis, at an angle different from the first configuration; and
a slit through which the wire protrudes,
wherein the wire comprises
a flat segment having a flat cross-sectional shape, and
a flexible segment located at a proximal end of the flat segment and having a bending rigidity lower than a minimum bending rigidity of the flat segment, and a length of the flat segment in a longitudinal direction is greater than a length of a long side of the slit.

* * * * *